(12) United States Patent
El-Aneed et al.

(10) Patent No.: US 9,012,838 B2
(45) Date of Patent: Apr. 21, 2015

(54) COVALENTLY FUNCTIONALIZED NANODIAMOND-BASED MALDI MATRICES AND METHODS OF USE THEREOF

(71) Applicant: University of Saskatchewan, Saskatoon (CA)

(72) Inventors: Anas El-Aneed, Saskatoon (CA); Jackson Chitanda, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 14/257,412

(22) Filed: Apr. 21, 2014

(65) Prior Publication Data

US 2014/0312218 A1  Oct. 23, 2014

Related U.S. Application Data

(60) Provisional application No. 61/813,913, filed on Apr. 19, 2013, provisional application No. 61/847,256, filed on Jul. 17, 2013.

(30) Foreign Application Priority Data

Jul. 17, 2013 (CA) .................................... 2821348

(51) Int. Cl.
| | | |
|---|---|---|
| *B01D 39/02* | (2006.01) | |
| *B32B 5/16* | (2006.01) | |
| *B05D 7/00* | (2006.01) | |
| *C08F 2/46* | (2006.01) | |
| *C07C 59/68* | (2006.01) | |
| *C07C 255/41* | (2006.01) | |
| *C07C 59/52* | (2006.01) | |
| *H01J 49/00* | (2006.01) | |
| *A61K 31/196* | (2006.01) | |
| *A61K 31/4172* | (2006.01) | |
| *A61K 47/48* | (2006.01) | |
| *A61K 48/00* | (2006.01) | |
| *C12N 15/113* | (2010.01) | |
| *C01B 31/06* | (2006.01) | |
| *B82Y 5/00* | (2011.01) | |

(52) U.S. Cl.
CPC .............. *C07C 59/68* (2013.01); *C07C 255/41* (2013.01); *C07C 59/52* (2013.01); *H01J 49/0027* (2013.01); *A61K 31/196* (2013.01); *A61K 31/4172* (2013.01); *A61K 47/48884* (2013.01); *A61K 48/0008* (2013.01); *C12N 15/113* (2013.01); *C01B 31/065* (2013.01); *C07B 2200/11* (2013.01); *C07C 2104/00* (2013.01); *B82Y 5/00* (2013.01)

(58) Field of Classification Search
USPC .................. 166/265, 228; 210/506; 435/6.12; 436/94, 501; 606/304
See application file for complete search history.

(56) References Cited

U.S. PATENT DOCUMENTS

| | | | |
|---|---|---|---|
| 7,326,837 B2 * | 2/2008 | Han et al. ...................... | 435/6.12 |
| 2005/0158549 A1 | 7/2005 | Khabashesku et al. | |
| 2006/0154259 A1 * | 7/2006 | Chang et al. ....................... | 435/6 |
| 2009/0218276 A1 * | 9/2009 | Linford et al. ................ | 210/506 |
| 2009/0226495 A1 | 9/2009 | Picardi | |
| 2009/0246887 A1 * | 10/2009 | Chang et al. ................... | 436/501 |
| 2011/0006218 A1 | 1/2011 | Mochalin et al. | |
| 2011/0008447 A1 * | 1/2011 | Chao et al. ..................... | 424/489 |
| 2011/0252713 A1 | 10/2011 | Chakraborty et al. | |
| 2012/0034464 A1 * | 2/2012 | Chakraborty et al. ......... | 428/402 |
| 2012/0271361 A1 * | 10/2012 | Zhou et al. ..................... | 606/304 |
| 2013/0014944 A1 * | 1/2013 | Mazyar et al. ................ | 166/265 |
| 2013/0081335 A1 * | 4/2013 | Mazyar et al. ................... | 51/309 |
| 2013/0102084 A1 * | 4/2013 | Loh et al. ......................... | 436/94 |
| 2013/0175026 A1 * | 7/2013 | Chakraborty et al. ......... | 166/228 |

FOREIGN PATENT DOCUMENTS

| | | |
|---|---|---|
| CA | 2692017 | 3/2009 |
| CA | 2795932 | 10/2011 |
| CA | 2796057 | 10/2011 |
| WO | 2011130023 | 10/2011 |
| WO | WO 2011/130023 A2 | 10/2011 |

OTHER PUBLICATIONS

Krueger, Anke et al, "Bitonylated Nanodiamond: Simple and Efficient Functionalization of Detonation Diamond", Langmuir, 2008, 24(8), pp. 4200-4204, Mar. 1, 2008.
Liu, Yu, et al., "Functionalization of Nanoscale Diamond Powder: Fluoro- Alkyl-, Amino-, and Amino Acid-Nanodiamond Derivatives", Chem. Mater., 2004, 16(2)), pp. 3294-3930, Sep. 2, 2004.
Cohen, Lucinda H., et al., "Small Molecule Analysis by MALDI Mass Spectrometry", Anal Bioanal Chem. 2002, 373, pp. 571-586.
Cohen, Lucinda, et al., "Small-Molecule Desorption/Ionization Mass Analysis", MALDI MS, A Practical Guide to Instrumentation, Methods and Applications, 2007, pp. 299-337.
Kaur, Randeep, et al, "Lysine-functionalized nanodiamonds: synthesis, physiochemical characterization, and nucleic acid binding studies", International Journal of Nanomedicine, 2012:7, pp. 3851-3866.
Kaur, Randeep, et al., "Nanodiamonds as novel nanomaterials for biomedical applications: drug delivery and imaging systems", International Journal of Nanomedicine, 2013:8, pp. 203-220.
Pham, M.D., et al, "Improved Mass Spectrometic Analysis of Membrane Proteins based on Rapid and Versatile Sample Preparation on Nanodiamond Particles", Analytical Chemistry, vol. 85, Issue 14, Jul. 16, 2013, pp. 6748-6755.

* cited by examiner

*Primary Examiner* — David A Vanore
(74) *Attorney, Agent, or Firm* — Bereskin & Parr LLP/S.E.N.C.R.L., s.r.l.; Patricia Folkins

(57) ABSTRACT

The present disclosure relates to functionalized nanodiamonds comprising at least one MALDI matrix covalently bonded to a nanodiamond and compositions comprising the same. The present disclosure also relates to methods of performing matrix-assisted laser desorption/ionization-mass spectrometry (MALDI-MS), for example on small molecules, using matrices comprising at least one MALDI matrix covalently bonded to a nanodiamond.

20 Claims, No Drawings

COVALENTLY FUNCTIONALIZED NANODIAMOND-BASED MALDI MATRICES AND METHODS OF USE THEREOF

CROSS-REFERENCE TO RELATED APPLICATIONS

The present application claims the benefit of priority from co-pending U.S. provisional application Nos. 61/813,913 and 61/847,256 filed on Apr. 19, 2013 and Jul. 17, 2013, respectively, and Canadian patent application no. 2,821,348 filed on Jul. 17, 2013, the contents of each of which are incorporated herein by reference in their entirety.

FIELD

The present disclosure generally relates to covalently functionalized nanodiamond-based MALDI matrices and to methods of performing MALDI-mass spectrometry (MS) using the same. In particular, the present disclosure relates to functionalized nanodiamonds comprising at least one MALDI matrix covalently bonded to a nanodiamond and to methods of performing MALDI-MS, for example on small molecules, using matrices comprising the same.

BACKGROUND

Matrix-assisted laser desorption/ionization-mass spectrometry (MALDI-MS) is a soft ionization method that is widely used in the analysis of large biomolecules such as proteins. An advantage for this technique is the production of singly charged species as this simplifies the analysis of large molecules. Although MALDI-MS has revolutionized the way high-molecular weight compounds are identified, small molecule identification has lagged behind. This is due to the fact that the majority of conventional matrices are small organic molecules, which interfere with the analysis of low-molecular weight (<1000 Da) compounds. Consequently, there is a need to design matrices that would reduce the matrix-background noise and/or increase the signal to noise ratio in the lower mass range.[1,2]

Detonation nanodiamonds (NDs) are produced by detonation of 2,4,6-trinitrotoluene (TNT) and Hexogen (RDX) in a closed system in the absence of oxygen. Nanodiamonds have a very narrow molecular distribution and an average diameter of about 4-5 nm. Additionally, they have excellent optical and mechanical properties. Depending on the quenching method used, the nanodiamond surface may have a variety of functional groups which upon oxidation give carboxylated nanodiamonds (Scheme 1). On the other hand, reduction processes introduce hydroxyl groups on the surface, as shown below in Scheme 1. Such oxidized or reduced forms of the nanodiamonds allow for variation in the possibilities of what can be grafted on the nanodiamond surface.[3,4]

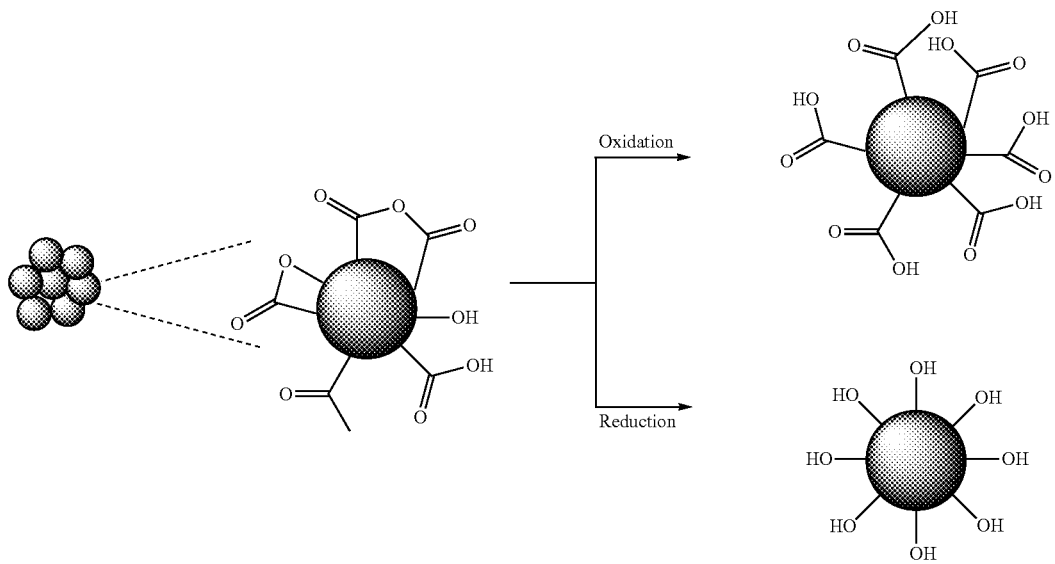

SUMMARY

A procedure for covalently bonding MALDI matrices to detonated nanodiamonds (ND) has been developed. The covalently functionalized nanodiamonds have been shown to be effective matrixes in the qualitative analysis of small molecule analytes using MALDI-MS.

Accordingly, the present disclosure includes a functionalized nanodiamond, comprising at least one compound that is a MALDI matrix covalently linked to a nanodiamond.

The present disclosure also includes a nanodiamond-based composition comprising a nanodiamond that is covalently linked to at least one MALDI matrix. In an embodiment, the nanodiamond-based composition is a MALDI-MS composition.

The present disclosure also includes a method of performing MALDI-MS, comprising:
  depositing (1) a matrix comprising at least one functionalized nanodiamond of the present disclosure, or a nanodiamond-based composition of the present disclosure, and (2) at least one sample, on a MALDI substrate; and
  performing MALDI-MS.

Also included is a use of the functionalized nanodiamonds of the present disclosure, or a composition comprising the functionalized nanodiamonds of the present disclosure, for MALDI-MS.

Other features and advantages of the present application will become apparent from the following detailed description. It should be understood; however, that the scope of the claims should not be limited by the embodiments set forth in the examples, but should be given the broadest interpretation consistent with the description as a whole.

DETAILED DESCRIPTION

I. Definitions

Unless otherwise indicated, the definitions and embodiments described in this and other sections are intended to be applicable to all embodiments and aspects of the disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular molecule, material and/or conditions would depend on the specific synthetic manipulation to be performed, and the identity of the molecule(s) and/or material(s) to be transformed, but the selection would be well within the skill of a person trained in the art. All synthetic process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a MALDI matrix" should be understood to present certain aspects with one MALDI matrix, or two or more additional MALDI matrices.

In embodiments comprising an "additional" or "second" component, such as an additional or second MALDI matrix, the second component as used herein is chemically different from the other components or first component. A "third" component is different from the other, first, and second components, and further enumerated or "additional" components are similarly different.

In embodiments of the present disclosure, the MALDI matrices described herein have at least one asymmetric center. These MALDI matrices exist as enantiomers. Where MALDI matrices possess more than one asymmetric center, they may exist as diastereomers. It is to be understood that all such isomers and mixtures thereof in any proportion are encompassed within the scope of the present disclosure. It is to be further understood that while the stereochemistry of the MALDI matrix may be as shown in any given MALDI matrix listed herein, such MALDI matrices may also contain certain amounts (e.g. less than 20%, suitably less than 10%, more suitably less than 5%) of MALDI matrices having alternate stereochemistry. For example, MALDI matrices that are shown without any stereochemical designations are understood to be racemic mixtures (i.e. contain an equal amount of each possible enantiomer or diastereomer). However, it is to be understood that all enantiomers and diastereomers are included within the scope of the present disclosure, including mixtures thereof in any proportion.

The term "covalently functionalized nanodiamond-based matrix" or "functionalized nanodiamond matrix" and the like as used herein refers to a matrix comprising at least one MALDI matrix covalently linked to the surface of a nanodiamond.

The term "MALDI matrix" as used herein refers to any molecule or material that is suitable as a matrix for use in MALDI-MS. The identification of suitable matrix materials is, for example, based on the following molecular design considerations:

(i) they are of a fairly low molecular weight (to allow facile vaporization), but are large enough (with a low enough vapor pressure) not to evaporate during sample preparation or while standing in the spectrometer;

(ii) they are often acidic, therefore act as a proton source to encourage ionization of the analyte; however basic matrices are also suitable;

(iii) they often have a strong optical absorption in either the UV or IR range so that they rapidly and efficiently absorb laser irradiation. This efficiency is commonly associated with chemical structures incorporating several conjugated double bonds;

(iv) they are often functionalized with polar groups, allowing their use in aqueous solutions; and (v) they typically contain a chromophore.

Other design considerations and suitable MALDI matrixes are known in the art (see for example, references 1 and 2). The present disclosure includes MALDI matrixes that are known in the art as well as molecules and materials that are not known in the art to act as such, yet are shown to function as a MALDI matrix.

The term "covalently linked" as used herein means that the surface of the nanodiamond comprises at least one compound that is a MALDI matrix attached thereto via at least one covalent linkage. In an embodiment, the MALDI matrix is covalently bonded to the nanodiamond via an ester or amide linkage:

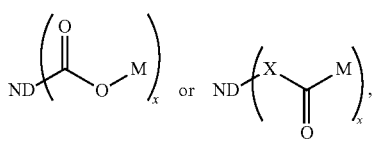

wherein ND represents the nanodiamond, X is O or NH, M represents the MALDI matrix and x is an integer that is greater than zero representing the number of groups bonded to the nanodiamond. The selection of a suitable synthetic route to obtain an ester or amide linkage can be made by a person skilled in the art. A number of synthetic routes are known in the art, for example as described in Smith, M. B. and March J., "March's Advanced Organic Chemistry: Reactions, Mechanisms and Structure" 5th ed., John Wiley & Sons, Inc., 2001 (New York) at, for example, pages 482-486 and pages 506-510. In another embodiment, the at least one MALDI matrix is covalently bonded to the nanodiamond via a linker group. In an embodiment, the linker group comprises at least one ester or amide linkage although a person skilled in the art would appreciate that other linking functional groups, such as ethers, thioethers, thioamides, thioesters and/or amines can additionally, or alternatively, be present. In a further embodiment, the linker group also comprises one or more $C_1$-$C_{20}$alkylene groups, such groups being either straight chain or branched chain alkylene groups. In another embodiment, when more than one MALDI matrix is present, each MALDI matrix is attached to the ND via its own linker or two or more MALDI matrices are attached to the ND via the same linker. In an embodiment, the nanodiamonds are functionalized with MALDI matrices in a monolayer or multilayer arrangement.

The term "naturally occurring amino acid" as used herein refers to an organic compound comprising amine (—$NH_2$) and carboxylic acid (—COOH) functional groups, along with a side-chain specific to each amino acid. The key elements of an amino acid are carbon, hydrogen, oxygen and nitrogen, though other elements are found in the side-chains of certain amino acids, including S and Se. About 500 amino acids are known in nature[5]. They can be classified, for example, according to the core structural functional groups' locations as alpha ($\alpha$), beta ($\beta$), gamma ($\gamma$) or delta ($\delta$), amino acids; other categories relate to polarity, pH level, and side-chain group type (e.g. acidic, basic, neutral, aliphatic, acyclic, aromatic, containing hydroxyl or sulfur, etc.). In an embodiment, the naturally occurring amino acid is one of the 23 proteinogenic amino acids, that is, amino acids that are precursors to proteins, and are incorporated into proteins during translation.

The term "naturally occurring basic amino acid" as used herein refers to a naturally occurring amino acid, having a side chain comprising a basic group (i.e. can accept hydrogen ions). It will be appreciated by a person skilled in the art that whether a basic group exists in a protonated or deprotonated form depends, for example on the $pK_a$ of the basic group. In an embodiment, at least one basic group of the basic amino acid has been converted to its corresponding acid addition salt. Naturally occurring basic amino acids include, for example, arginine, histidine and lysine.

The term "naturally occurring acidic amino acid" as used herein refers to a naturally occurring amino acid, having a side chain comprising an acidic group (i.e. can donate hydrogen ions). It will be appreciated by a person skilled in the art that whether an acidic group exists in a protonated or deprotonated form depends, for example on the $pK_a$ of the acidic group. In an embodiment, at least one acid group of the acidic amino acid has been converted to its corresponding basic addition salt. Naturally occurring acid amino acids include, for example, aspartic acid and glutamic acid.

The term "naturally occurring neutral amino acid" as used herein refers to a naturally occurring amino acid, having a side chain comprising an neutral group (a group that neither accepts or donates protons). Naturally occurring neutral amino acids include, for example, glycine, alanine, valine, phenylalanine, isoleucine, leucine, methionine, tyrosine and tryptophan.

The term "amino acid derivative" as used herein refers to a naturally occurring amino acid, or an analog thereof, containing a modified functional group, such as a naturally occurring amino acid, or analog thereof, in which the amino group, the carboxyl group and/or a side chain function group has been derivatized. Examples of such groups include, but are not limited to, $C_{1-10}$alkyl-, aryl- and $C_{1-6}$alkylenearyl-functionalized amines, carboxylic acids, hydroxyls, thiols and/or amides, including di-functionalization of a group where possible (for example amines and amides). In a further embodiment, such groups include methyl-, ethyl, aryl- and benzyl-functionalized carboxylic acids, hydroxyls and/or thiols and/or methyl-, dimethyl-, ethyl-, diethyl, aryl-, diaryl, benzyl and dibenzyl-functionalized amines and/or amides. Amino acid derivatives are either naturally occurring or are synthetic.

The term "amino acid analog" as used herein refers to a naturally occurring amino acid, or a derivative thereof, in which one or more of the functional groups have been modified, for example oxidized, reduced, functionalized or removed, replaced with a functionally similar functional group, or moved to a different location on the amino acid molecule. Examples of such compounds are well known and studied in the art, and include, for example, β-amino acids, fluorinated amino acids and α-hydroxy analogs. Amino acid analogs are either naturally occurring or are synthetic.

The term "CHCA" as used herein refers to α-cyano-4-hydroxycinnamic acid:

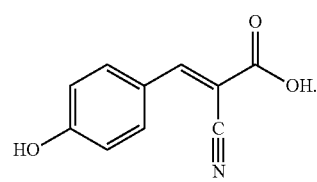 [SMILES: N#C/C(=C\c1ccc(O)cc1)C(=O)O]

The term "DNB" as used herein refers to 2,4-dihydroxybenzoic acid:

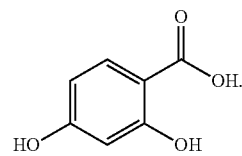

The term "SA" as used herein refers to sinapinic acid, which is the compound 3,5-dimethoxy-4-hydroxycinnamic acid:

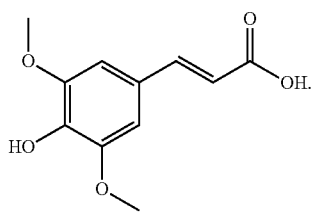 [SMILES: COc1cc(/C=C/C(=O)O)cc(OC)c1O]

The term "MeOH" as used herein refers to methanol.
The term "ACN" as used herein refers to acetonitrile.
The term "DMF" as used herein refers to dimethylformamide.
The term "TFA" as used herein refers to trifluoroacetic acid:

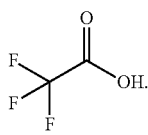

The term "TC" as used herein refers to tetracycline:

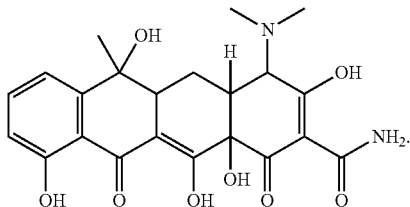 [SMILES: CN(C)C1C(O)=C(C(N)=O)C(=O)C2(O)C(O)=C3C(=O)c4c(O)cccc4C(C)(O)C3CC12]

The term "ER" as used herein refers to erythromycin:

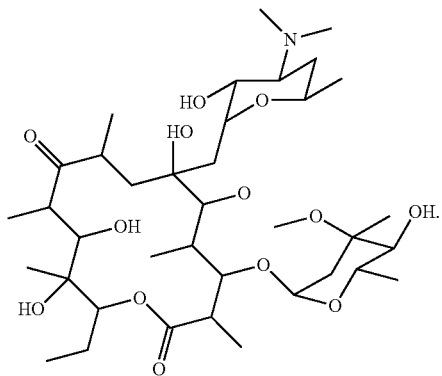 [SMILES: CCC1OC(=O)C(C)C(OC2CC(C)(OC)C(O)C(C)O2)C(C)C(O)C(O)(CC2OC(C)CC(N(C)C)C2O)CC(C)C(=O)C(C)C(O)C1(C)O]

The term "QN" as used herein refers to quinine:

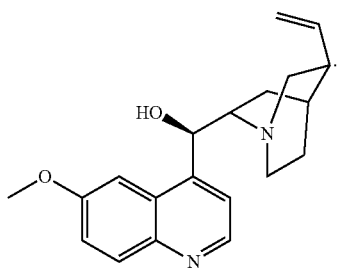 [SMILES: C=CC1CN2CCC1CC2[C@H](O)c1ccnc2ccc(OC)cc12]

The term "PX" as used herein refers to piroxicam:

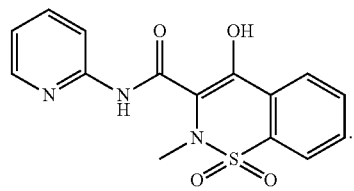 [SMILES: CN1C(C(=O)Nc2ccccn2)=C(O)c2ccccc2S1(=O)=O]

The term "PD" as used herein refers to prednisolone:

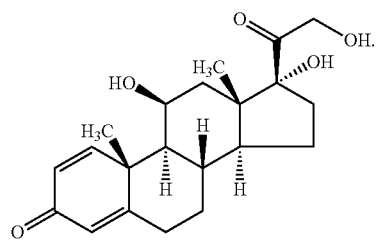

The term "MP" as used herein refers to melphalan:

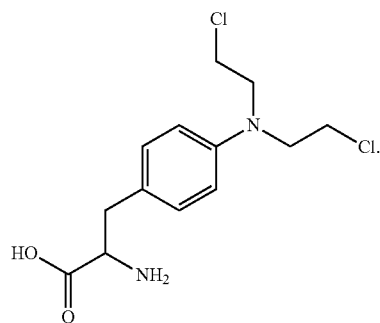 [SMILES: NC(Cc1ccc(N(CCCl)CCCl)cc1)C(=O)O]

The term "HP" as used herein refers to hesperetine:

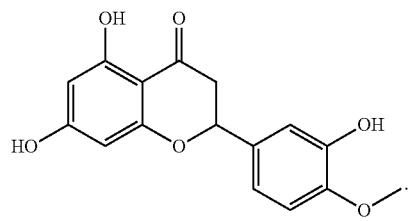 [SMILES: COc1ccc(C2CC(=O)c3c(O)cc(O)cc3O2)cc1O]

The term "LG" as used herein refers to luteolin-7-O-glucoside:

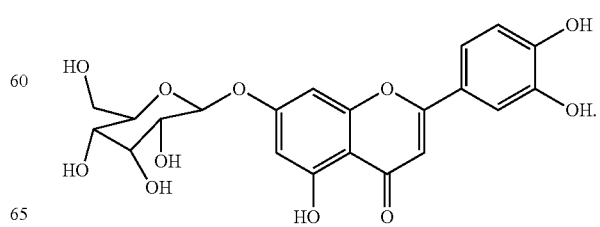

The term "RP" as used herein refers to reserpine:

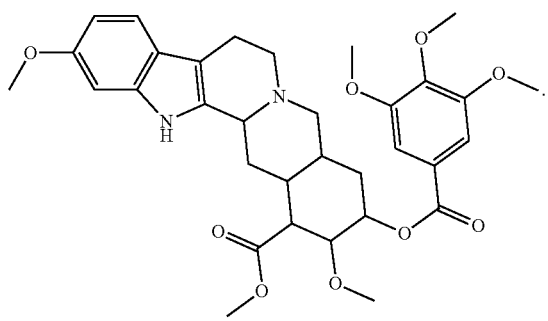

The term "LE" as used herein refers to leucine-enkephalin:

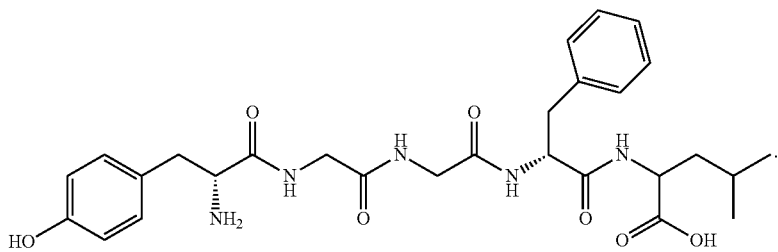 [SMILES: CC(C)CC(NC(=O)[C@@H](Cc1ccccc1)NC(=O)CNC(=O)CNC(=O)[C@H](N)Cc1ccc(O)cc1)C(=O)O]

The term "LYS" as used herein refers to the compound 2,6-diamino-N-(3-aminopropyl)hexanamide:

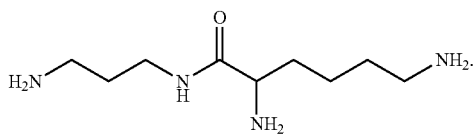 [SMILES: NCCCCC(N)C(=O)NCCCN]

The terms "ND-SA" or "nanodiamond-sinapinic acid" as used herein refer to a matrix comprising at least one sinapinic acid covalently bonded via an ester linkage to a nanodiamond, represent schematically as:

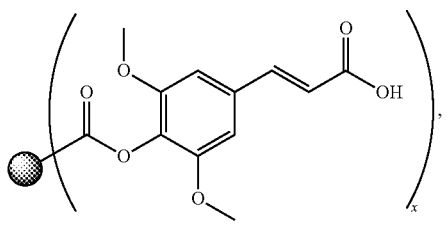

wherein x is an integer that is greater than zero representing the number of sinapinic acid groups bonded to the nanodiamond.

The terms "ND-CHCA" or "nanodiamond-α-cyano-4-hydroxycinnamic acid" as used herein refer to a matrix comprising at least one α-cyano-4-hydroxycinnamic acid covalently bonded via an ester linkage to a nanodiamond represented schematically as:

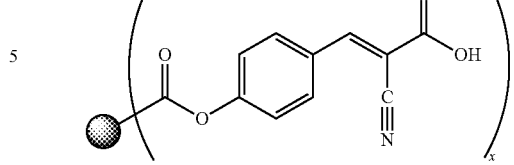

wherein x is an integer that is greater than zero representing the number of α-cyano-4-hydroxycinnamic acid groups bonded to the nanodiamond.

The terms "ND-DHB" or "nanodiamond-2,4-dihydroxybenzoic acid" as used herein refer to a matrix comprising at least one 2,4-dihydroxybenzoic acid covalently bonded via an ester linkage to a nanodiamond represented schematically as:

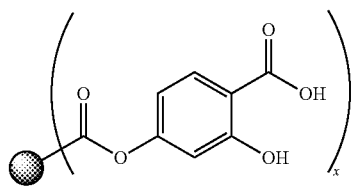

wherein x is an integer that is greater than zero representing the number of 2,4-dihydroxybenzoic acid groups bonded to the nanodiamond.

The term "ND-LYS" as used herein refers to a matrix comprising at least one lysine-based compound (2,6-diamino-N-(3-aminopropyl)hexanamide) covalently bonded via an amide linkage to a nanodiamond. The following schematic represents 2,6-diamino-N-(3-aminopropyl)hexanamide covalently attached via an amide linkage to a nanodiamond in one possible configuration:

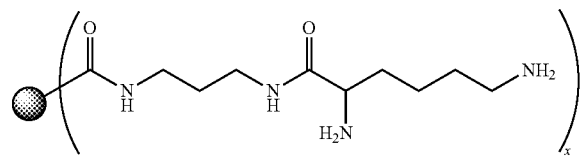

wherein x is an integer that is greater than zero representing the number of 2,6-diamino-N-(3-aminopropyl)hexanamide groups bonded to the nanodiamond.

Other possible configurations have one of the other two amino groups attached to the nanodiamond. The molecule may be a mixture of all three possible configurations. The configurations where a primary amino group (i.e. the amino groups located at each end of the molecule) is attached to the nanodiamond may represent the major species.

The term "ND-COOH" as used herein refers to a carboxylated nanodiamond, represented by the following schematic:

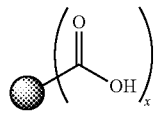

wherein x is an integer that is greater than zero representing the number of carboxylic acid groups bonded to the nanodiamond.

A person skilled in the art would appreciate that a plurality of MALDI matrices will be covalently attached to the ND surface i.e. that x is an integer representing the number of such groups on the nanodiamond. This number will depend on the conditions for activation of the detonation nanodiamonds and the size of the nanodiamond as would be understood by a person skilled in the art.

The term "nanodiamond-based" composition as used herein, means that the composition comprises a nanodiamond.

The term "nanodiamond" or "ND" as used herein refers to a diamond particles having an average particle size of less than about 1 μm. "Average particle size" refers to the number average particle size based on the largest linear dimension of the particle (usually referred to as diameter). In an embodiment, the nanodiamonds have an average particle size of about 1 nm to 250 nm or less. In a further embodiment, the nanodiamonds have an average particle size of about 1 nm to about 10 nm.

The term "spotting" as used herein refers to depositing a sample, such as a liquid or solution, onto a surface in the form of a spot. Spotting is typically done with a pipette or needle and can be automated using known computer-controlled automated spotting devices. In an embodiment the surface is a MALDI plate or any other surface or substrate on which a MALDI-MS technique is performed. For example, another surface is a tissue surface and the technique that is performed is MALDI imaging.

The term "MALDI" and "MALDI-MS" as used herein refers to matrix-assisted laser desorption/ionization and matrix-assisted laser desorption/ionization mass spectrometry, respectively and refers to any technique that involves the use of MALDI or MALDI-MS, including, for example, MALDI-MS/MS.

II. Functionalized Nanodiamonds and their Compositions

MALDI-MS uses matrices that allow for the ionization of tested analytes. In the lower mass range (less than about 1000 Da), conventional organic matrices can interfere with the analysis due to, for example significant background noise. In the present disclosure, nanodiamonds covalently linked to molecules that act as MALDI matrices were prepared and successfully used in the MALDI-MS analysis of non-protein-based, smaller organic compounds.

Accordingly, the present disclosure includes a functionalized nanodiamond, comprising at least one compound that is a MALDI matrix covalently linked to a nanodiamond.

In an embodiment, the nanodiamonds used to prepare the functionalized nanodiamonds of the present application are detonated nanodiamonds which have been treated under oxidative or reductive conditions. In a further embodiment, the nanodiamonds are detonated nanodiamonds which have been treated under oxidative conditions to provide carboxylated nanodiamonds (ND-COOH). In a further embodiment the nanodiamonds have a average particle size of about 1 nm to about 10 nm, about 3 nm to about 6 nm, or about 4 nm to about 5 nm. In a further embodiment, the carboxylated nanodiamonds have a Zeta potential of about −40 V to about −50 V, or about −45 V.

In an embodiment, the MALDI matrix is covalently linked to the nanodiamond via an ester linkage. For example, a suitable nanodiamond is reacted with a suitable MALDI matrix under conditions to obtain an ester linkage. In an embodiment, the conditions to obtain the ester linkage comprise treating a carboxylated nanodiamond (ND-COOH) under conditions to activate the carboxylic acid, for example by conversion to the acid chloride (ND-COCl) or by reaction with a carboxylic acid activating reagent to provide a nanodiamond of the formula ND-CO-A, wherein A is an activating group for a carboxylic acid, followed by nucleophilic displacement of the chloride or A group with an oxygen nucleophile (such as a hydroxyl group) on the MALDI matrix. Carboxylic acid activating reagents are well known in the art and include, for example, well known peptide coupling reagents such as dicyclohexylcarbodiimide (DCC), diisopropylcarbodiimide, hydroxybenzotriazole (HOBT), (Benzotriazol-1-yloxy)tris(dimethylamino)phosphonium hexafluorophosphate (BOP), [N,N,N',N'-tetramethyl-O-(7-azabenzotriazol-1-yl)uronium hexafluorophosphate (HATU) and the like. A person skilled in the art would appreciate that an ester linkage is also available using the same reaction conditions, but, in the alternative, reacting a detonated nanodiamond that has been treated under reductive conditions to provide a hydroxylated nanodiamond (ND-OH), with a MALDI matrix comprising an activated carboxylic acid.

In an embodiment, the MALDI matrix is covalently linked to the nanodiamond via an amide linkage. For example, a suitable nanodiamond is reacted with a suitable MALDI matrix under conditions to obtain an amide linkage. In an embodiment, the conditions to obtain the amide linkage comprise treating a carboxylated nanodiamond (ND-COOH) under conditions to activate the carboxylic acid, for example by conversion to the acid chloride (ND-COCl) or by reaction with a carboxylic acid activating reagent to provide a nanodiamond of the formula ND-CO-A, wherein A is an activating group for a carboxylic acid, followed by nucleophilic displacement of the chloride or A group with a nitrogen nucleophile (such as an amino group) on the MALDI matrix. Carboxylic acid activating reagents are well known in the art and include, for example, well known peptide coupling reagents such as dicyclohexylcarbodiimide (DCC), diisopropylcarbodiimide, hydroxybenzotriazole (HOBT), (Benzotriazol-1-yloxy)tris(dimethylamino)phosphonium hexafluorophosphate (BOP), [N,N,N',N'-tetramethyl-O-(7-azabenzotriazol-1-yl)uronium hexafluorophosphate (HATU) and the like. A person skilled in the art would appreciate that an ester linkage is also available using the same reaction conditions, but, in the alternative, reacting a detonated nanodiamond that has been treated under conditions to provide a amino-substituted nanodiamond (ND-NH$_2$), with a MALDI matrix comprising an activated carboxylic acid.

In an embodiment, the MALDI matrix is covalently linked to the nanodiamond via a linker group. In an embodiment, the linker group comprises one or more $C_1$-$C_{20}$alkylene groups, such groups being either straight chain or branched chain alkylene groups. In an embodiment, the MALDI matrix is covalently linked to the nanodiamond via a linker group comprising a $C_{1-6}$alkylene group. In another embodiment, the MALDI matrix is covalently linked to the nanodiamond via a linker group comprising a propylene group. In an embodiment, the linker group is linked to the MALDI matrix via at least one ester or amide linkage although a person skilled in the art would appreciate that other linker groups, such as ethers, thioethers, thioamides, thioesters and/or amines is additionally, or alternatively, present. It is an embodiment that the linker group is linked to the MALDI matrix via an amide linkage.

In embodiment, the MALDI matrix is a cinnamic acid, a hydroxylated benzoic acid derivative, an aromatic carbonyl derivative, an aromatic amine, an aliphatic amine, a naturally occurring amino acid, an analog of a naturally occurring amino acid, a derivative of a naturally occurring amino acid, a peptide comprising 2 to 10, or 2 to 6, naturally occurring amino acids, a peptide comprising 2 to 10, or 2 to 6, naturally occurring amino acids of which at least one is an analog of a naturally occurring amino acid, and a peptide comprising 2 to 10, or 2 to 6, naturally occurring amino acids of which at least one is an derivative of a naturally occurring amino acid, or, where possible, a salt thereof.

In a further embodiment, the MALDI matrix is selected from the group consisting of sinapinic acid (3,5-dimethoxy-4-hydroxycinnamic acid), α-cyano-4-hydroxycinnamic acid, 2,4-dihydroxybenzoic acid, 2,6-diamino-N-(3-aminopropyl) hexanamide, 2,5-dihydroxybenzoic acid, nicotinic acid, ferulic acid (4-hydroxy-3-methoxycinnamic acid), caffeic acid, 3-hydroxypicolinic acid, picolinic acid, 2-amino-4-methyl-5-nitropyridine, 2-amino-5-nitropyridine, 2-iodoacetamide, 2,4,6-trihydroxyacetophenone, 2,6-dihydroxyacetophenone, 1,5-diaminonaphthalene, 2-(4'-hydroxybenzeneazo)benzoic acid, 2-mercaptobenzothiazole, 4-chloro-α-cyanocinnamic acid and α-cyano-4-fluorocinnamic acid. In another embodiment, the organic MALDI matrix is selected from the group consisting of sinapinic acid, α-cyano-4-hydroxycinnamic acid, 2,4-dihydroxybenzoic acid and 2,6-diamino-N-(3-aminopropyl)hexanamide.

In an embodiment, the MALDI matrix is a naturally occurring amino acid or an analog or derivative of a naturally occurring amino acid, or a salt thereof. In a further embodiment, the naturally occurring amino acid is a naturally occurring basic amino acid, or an analog or derivative of a naturally occurring basic amino acid, or an acid addition salt thereof. In a further embodiment, the naturally occurring basic amino acid is selected from histidine and lysine, and an analog or derivative thereof, or an acid addition salt thereof.

In an embodiment, the naturally occurring amino acid, or analog or derivative thereof, is covalently linked to the nanodiamond via a linker group. In an embodiment, the linker group comprises one or more $C_1$-$C_{20}$alkylene groups, such groups being either straight chain or branched chain alkylene groups. In an embodiment, the amino acid is covalently linked to the nanodiamond via a linker group comprising a $C_{1-6}$alkylene group. In another embodiment, the amino acid is covalently linked to the nanodiamond via a linker group comprising a propylene group. In an embodiment, the linker group is linked to amino acid via at least one ester or amide linkage although a person skilled in the art would appreciate that other linker groups, such as ethers, thioethers, thioamides, thioesters and/or amines is additionally, or alternatively, present. It is an embodiment that the linker group is linked to the amino acid via an amide linkage.

In an embodiment, the naturally occurring amino acid and the linker group together form the structure:

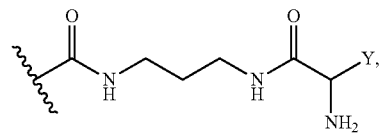

wherein Y is the side chain of a naturally occurring amino acid, or an acid addition salt thereof. In an embodiment, Y is selected from —$(CH_2)_4NH_2$,

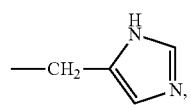

and —$(CH_2)_3NHC(NH)NH_2$.

In another embodiment, the naturally occurring amino acid and the linker group together form the structure:

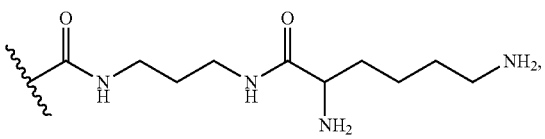 [SMILES: *C(=O)NCCCNC(=O)C(N)CCCCN]

or an acid addition salt thereof.

In an embodiment, the MALDI matrix is a naturally occurring dipeptide or an analog or derivative of a naturally occurring dipeptide, or a salt thereof. In a further embodiment, the naturally occurring dipeptide comprises at least one naturally occurring basic amino acid, or an analog or derivative of a naturally occurring basic amino acid, or an acid addition salt thereof. In a further embodiment, the naturally occurring basic amino acid is selected from one or more of histidine and lysine, and an analog or derivative thereof, or an acid addition salt thereof.

In an embodiment, the naturally occurring dipeptide, or analog or derivative thereof, is covalently linked to the nanodiamond via a linker group. In an embodiment, the linker group comprises one or more $C_1$-$C_{20}$alkylene groups, such groups being either straight chain or branched chain alkylene groups. In an embodiment, the dipeptide is covalently linked to the nanodiamond via a linker group comprising a $C_{1-6}$alkylene group. In another embodiment, the dipeptide is covalently linked to the nanodiamond via a linker group comprising a propylene group. In an embodiment, the linker group is linked to the dipeptide via at least one ester or amide linkage although a person skilled in the art would appreciate that other linker groups, such as ethers, thioethers, thioamides, thioesters and/or amines is additionally, or alternatively, present. It is an embodiment that the linker group is linked to the dipeptide via an amide linkage.

In another embodiment, the naturally occurring dipeptide and the linker group together form the structure:

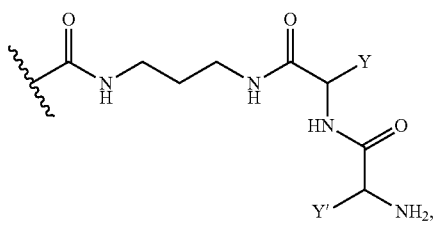

wherein Y and Y' are, independently, the side chain of a naturally occurring amino acid, or an acid addition salt thereof. In an embodiment, Y and Y' are independently selected from —$(CH_2)_4NH_2$,

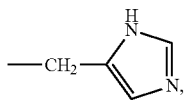

and —$(CH_2)_3NHC(NH)NH_2$.

In another embodiment, the naturally occurring dipeptide and the linker group together form the structure:

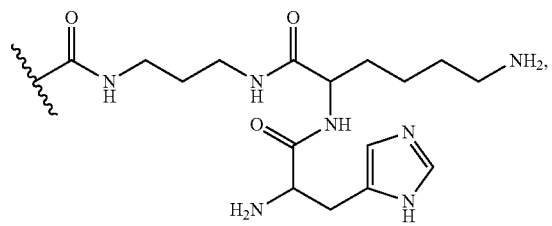 [SMILES: *C(=O)NCCCNC(=O)C(CCCCN)NC(=O)C(N)Cc1cnc[nH]1]

or an acid addition salt thereof.

In an embodiment, the functionalized nanodiamonds of the present application comprise one, two, three, or more different types of MALDI matrices covalently bonded thereto. In further embodiment, the functionalized nanodiamonds of the present application comprise one or two different types of MALDI matrices covalently bonded. In an embodiment, when two or more different types of MALDI matrices are present, each different type of MALDI matrix, is covalently bonded to the nanodiamond in a sequential manner or at the same time. When bonding is performed in a sequential manner, there exists the possibility for layer-type arrangements.

The compounds that are MALDI matrices are either commercially available or are synthesized using methods known in the art.

The present disclosure also includes a nanodiamond-based composition comprising a nanodiamond that is covalently linked to at least one compound that is a MALDI matrix. In an embodiment, the nanodiamond-based composition is a MALDI-MS composition. In a further embodiment, the MALDI-MS composition comprises the functionalized ND of the present disclosure and one or more solvents. In an embodiment the one or more solvents comprise a mixture of water and an organic solvent or mixture of organic solvents, such as acetonitrile, methanol and/or ethanol. In a further embodiment, the MALDI-MS composition further comprises an acid, such as trifluoroacetic acid (TFA). In another embodiment, the ratio of water to organic solvent is 1:1 to 1:2. In a further embodiment, the TFA, if used, is present in an amount, based on the total amount of solvent, of about 0.5% (v/v) to about 5% (v/v), or about 1% (v/v). In an embodiment, the solvents are selected to allow dissolution of both hydrophobic and hydrophilic analytes. In another embodiment, the composition further comprises at least one sodium or potassium salt, for example from sodium or potassium chloride.

III. Methods

The functionalized nanodiamond-based matrices of the present disclosure were shown to facilitate the ionization of various small organic compounds during analysis by MALDI-MS. Advantages over the conventional matrices tested in the present studies were observed. For example, signal intensity was found to be enhanced in general when the functionalized nanodiamond-based matrices were used, in particular in comparison to the conventional matrices, and in particular in the negative ion-mode. The negative ion mode has an inherent advantage in terms of background noise but conventional matrices do not generally perform well in this mode. The functionalized nanodiamond-based matrices of the present disclosure provided useful results with the ability to ionize various structures, and background noise was reduced.

Accordingly, the present disclosure also includes a method of performing MALDI-MS, comprising:
depositing a matrix comprising (1) at least one functionalized nanodiamond of the present disclosure, or a nanodiamond-based composition of the present disclosure, and (2) at least one sample, on a MALDI substrate; and performing MALDI-MS.

In an embodiment, the sample comprises, consists essentially of or consists of at least one analyte that is a small molecule. In another embodiment, the sample comprises, consists essentially of or consists of at least one analyte having a molecular weight of less than about 1000 Da. In a further embodiment, the sample comprises, consists essentially of or consists of at least one analyte having a molecular weight of about 200 Da to about 1000 Da. It is an embodiment that the sample comprises, consists essentially of or consists of at least one analyte having a molecular weight of about 300 Da to about 750 Da.

In an embodiment, the MALDI-MS is performed in negative mode. In another embodiment, the MALDI-MS is performed in positive mode. In further embodiment, the MALDI-MS is performed using procedures well known to those skilled in the art.

In an embodiment, the matrix comprising at least one functionalized nanodiamond of the present disclosure or a nanodiamond-based composition of the present disclosure, is deposited on the MALDI substrate by spotting. In a further embodiment, about 0.1 µL to about 5 µL, about 0.5 µL to about 2 µL or about 1 µL of the matrix or the nanodiamond-based composition of the present disclosure is deposited. In an embodiment the at least one functionalized nanodiamond of the present disclosure, or the nanodiamond-based composition of the present disclosure, and the sample are deposited onto the MALDI substrate in any order and combination. For example at least one functionalized nanodiamond of the present disclosure, or the nanodiamond-based composition of the present disclosure, is deposited first, followed by depositing the sample on to the at least one functionalized nanodiamond of the present disclosure, or the nanodiamond-based composition of the present disclosure, or the sample is deposited first, followed by depositing the at least one functionalized nanodiamond of the present disclosure, or the nanodiamond-based composition of the present disclosure, on to the sample. In another example, the sample and the at least one functionalized nanodiamond of the present disclosure, or the nanodiamond-based composition of the present disclosure, are pre-mixed and deposited together. In yet another example the at least one functionalized nanodiamond of the present disclosure, or the nanodiamond-based composition of the present disclosure, and the sample are deposited in a layers in alternating or random fashion.

In a further embodiment, the composition is treated to remove aggregated NDs (for example by vortexing) prior to spotting. In a further embodiment, the spot of the nanodiamond-based composition is allowed to dry, for example at ambient or room temperature, prior to depositing the sample onto the matrix.

In an embodiment, the sample is deposited onto the matrix by spotting. In a further embodiment, about 0.1 µL to about 5 µL, about 0.5 µL to about 2 µL or about 1 µL of the sample is spotted onto the matrix. In a further embodiment, the sample comprises on or more analytes and the analytes are present in the sample at a concentration of about 1 µg/mL to 100 µg/mL, about 10 µg/mL to 30 µg/mL or about 20 µg/mL. In a further embodiment, the spot of the sample is allowed to dry, for example at ambient or room temperature, prior to performing MALDI-MS.

In an embodiment, the functionalized nanodiamond-based matrices of the present disclosure are used in a mass spectrometry instrument having a MALDI ionization source. For example, Bruker, AB Sciex, Waters, and Thermo Fisher produce MALDI ionization sources that are interfaced with mass spectrometry instruments. The selection of a MALDI ionization source for a particular mass spectrometry instrument is readily made by a person skilled in the art. In an embodiment, the mass spectrometry instrument is a MALDI-MS or a MALDI-MS/MS instrument.

Also included is a use of the functionalized nanodiamonds of the present disclosure, or a composition comprising the functionalized nanodiamonds of the present disclosure, for MALDI-MS.

The following non-limiting examples are illustrative of the present disclosure.

EXAMPLES

The functionalized nanodiamond-based MALDI matrices of the present disclosure take advantage of the optical properties of nanodiamonds and the ionization ability of conventional organic matrices, and are useful for the analysis of small molecules. The functionalized nanodiamond-based matrices maintain the desired properties of a good matrix including, for example forming a fine crystalline solid during deposition, for example, co-deposition with a sample comprising an analyte; efficiently absorbing at the wavelength of the laser so as to allow for ionization; and with minimum background noise at a lower mass range.

I. Matrix Design

Four covalently functionalized nanodiamond-based matrices were explored as matrices for MALDI-MS in the present studies. The three most common conventional organic MALDI matrices (sinapinic acid (SA), α-cyano-4-hydroxycinnamic acid (CHCA) and 2,4-dihydroxybenzoic acid (DHB)) were covalently bonded to nanodiamonds, using carboxylated nanodiamonds (ND-COOH) as the starting material, to obtain the following corresponding covalently functionalized nanodiamond-based matrices: nanodiamond-sinapinic acid (ND-SA), nanodiamond-α-cyano-4-hydroxycinnamic acid (ND-CHCA) and nanodiamond-2,4-dihydroxybenzoic acid (ND-DHB). In addition to these matrices, the lysine-based covalently functionalized nanodiamond-based matrix (ND-LYS) was also synthesized as described elsewhere.[6] Pristine carboxylated nanodiamonds (ND-COOH) as well as conventional organic matrices (DHB, CHCA and SA) were used as comparators in the present studies.

A total of five small-molecule analytes (mass range of about 324-733 Da) with varying molecular structures were selected from the 10 analytes shown in Table 1 for analysis by MALDI-MS using the covalently functionalized nanodiamond-based matrices of the present disclosure as a MALDI matrix. The selection of analytes was based on differences in structural functionality which provides possible ionization ability in both negative and positive ion modes.

II. Methods and Materials

Diamond nanoparticles, of diameter=4-5 nm and Zeta potential=-45 V, were obtained from International Technology Centre (Raleigh, N.C., USA). Chemicals used in the synthesis namely, α-cyano-4-hydroxycinnamic acid (CHCA), 2,4-dihydroxybenzoic acid (DHB), sinapinic acid (SA) and thionyl chloride were obtained from Sigma Aldrich (St. Louis, Mo.). Analytes: piroxicam (PX) tetracycline (TC), erythromycin (ER), quinine (QN), prednisolone (PD), melphalan (MP), luteolin-7-O-glucoside (LG), reserpine (RP), leucine-enkephalin (LE), and hesperetine (HP) powders were obtained from Extrasynthese (Genay, France). α-Cyano-4-hydroxycinnamic acid (CHCA) and sinapinic acid (SA) powder used as comparator matrices in the MALDI-MS were obtained from Waters (Milford, Mass.). 2,4-Dihydroxybenzoic acid (DHB) used as a comparator MALDI matrix was obtained from Ettan Chemicals (Uppsala, Sweden). All organic solvents used in sample preparation for the MALDI-MS analysis (methanol (MeOH) and acetonitrile (ACN)) were of analytical grade and were mass spec. compatible. ND-LYS was prepared in accordance with the procedure presented in Kaur et al., 2012.[6]

The AB Sciex 4800 MALDI TOF/TOF™ instrument was operated in MS reflector positive and negative mode. Laser intensity ranges from 5000-5300 (unless otherwise indicated) were used for the covalently functionalized nanodiamond-based matrices. The same laser intensity range (unless otherwise indicated) was used for the SA, CHCA and DHB matrices for comparison's sake. 400 shots were acquired per spot. Default calibration was utilized.

III. Synthesis of Covalently Functionalized Nanodiamond-Based Matrices

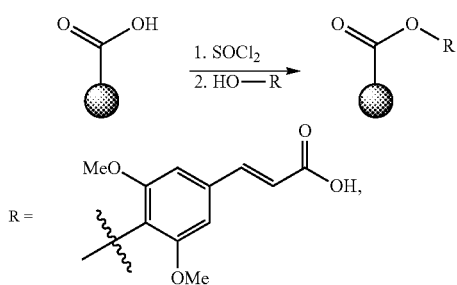

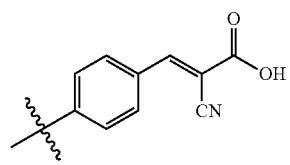

or

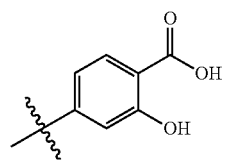

Sonication:

In order to disaggregate the nanodiamond particles, sonication was carried out, for 24 h in water and dimethyl formamide (DMF), in the presence of zirconium beads. Thereafter, Zeta potential and particle size were measured and found to be −45 mV and 4-5 nm, respectively.

Reaction:

Formation of ND-COCl: In a dry Schlenk flask, carboxylated nanodiamonds (0.100 g), zirconium beads (0.150 g) and DMF (10 mL) were added and sonicated. After 12 h, the DMF was pumped off to dryness using a vacuum pump. To the dried mixture, under nitrogen, excess thionyl chloride (6.0 mL) was added and sonicated for 24 h. Thereafter, the flask was placed on a 100° C. pre-heated oil bath. After refluxing the reaction for 24 h, it was let to cool to room temperature and then sonicated for 5 h before placing it back on the oil bath for an additional 24 h of refluxing. After cooling the reaction mixture to ambient temperature, excess thionyl chloride ($SOCl_2$) was removed under high vacuum.

Formation of ND-COO—R: To the dried ND-COCl/zirconium beads mixture, DMF (15 mL) and a respective organic matrix in large excess (500 mg) were added. The heterogeneous mixture was sonicated for 2 h then refluxed for 12 h at 100° C. Upon cooling, zirconium beads were removed by pipetting off the DMF solution mixture. The DMF solution mixture was centrifuged at 4° C. for 25 min (RCF=20 000). The supernatant was removed and DMF added to the residue. Before another centrifugation process, the mixture was sonicated for 1 h. After three successive centrifugation cycles in DMF, acetone was used for the last one. Finally, to the residue, water was added and sonicated for 2 h before it was lyophilized for 48 h. The final grayish powder was collected and analyzed by thermal gravimetric analysis (TGA). TGA profile showed the mass lost from the surface of the ND, to be larger than the one obtained from pristine ND. Moreover, the temperature at which the adsorbate was lost occurs at a different temperature.

IV. MALDI Analysis

General Sample Preparation:

A 1 mg/mL suspension of the desired nanodiamond-based matrix was prepared using a MeOH:$H_2O$:ACN (1:1:1) solvent mixture. This suspension was vortexed and sonicated for 30 min. Respective solutions of 20 μg/mL of each of the desired analytes were prepared in MeOH:ACN(1:1). Respective solutions of SA (ACN:MeOH, 1:1), CHCA (ACN:MeOH, 1:1) and DHB (ACN:$H_2O$, 1:1) were each prepared in 50 μL to a final concentration of 10 g/L each.

Spotting Method:

1 μL of the desired nanodiamond-based matrix was vortexed just before spotting and was spotted on the stainless-steel MALDI plate. After the spot had dried under ambient conditions, a 1 μL sample of 20 μg/mL of the desired analyte was spotted on top of the matrix and then left to dry. A similar procedure was followed for the SA, CHCA and DHB matrices as control samples, although vortexing was not required for the matrixes on their own.

IV. Results and Observations

See Table 2 for a summary of the analysis of five analytes using five nanodiamond-based matrices. See Table 3 for a summary of the analysis of five analytes using three conventional matrices.

A. Analysis of Piroxicam (PX) [331 Da]

Negative Ion Mode:

In the negative ion mode, [M−H]⁻ ions (m/z 330 Da) having at least moderate intensity were observed when each of the nanodiamond-based matrices was used. ND-LYS and ND-COOH showed greater ion count intensity and ND-SA, ND-DHB and ND-CHCA gave moderate [M−H]⁻ signals. All nanodiamond-based matrices gave a higher signal to noise ratio as compared to the conventional matrices (SA, CHCA and DHB), which gave a very weak to no [M−H]⁻ signal in the spectra obtained.

Positive Ion Mode:

The 331 Da [M+H]⁺ ion peak was weak in all nanodiamond-based matrices except the one from ND-SA, which gave an intense signal. All three conventional matrices gave an intense [M+H]⁺ signal. The nanodiamond-based matrices gave a good [M−H]⁻ peak signal and poor [M+H]⁺ signal in the positive mode, which was contrary to the conventional matrices.

B. Analysis of Tetracycline (TC) [444 Da]

Negative Ion Mode:

In the negative ion mode, [M−H]⁻ ions (m/z 443 Da) were detected when each of the nanodiamond-based matrices was used. It was observed that ND-CHCA gave the weakest [M−H]⁻ signal, while ND-COOH, ND-DHB, and ND-SA showed intense peaks. ND-LYS gave the highest ion count intensity with low background, and no inference from the matrix signals. The m/z 443 [M−H]⁻ ions were also observed in two (SA and DHB) of the three conventional matrices, however their spectra were characterized with a significant amount of matrix background noise and peak interference.

Positive Ion Mode:

The 445 Da [M+H]⁺ ion peak was observed in four (ND-SA, ND-CHCA, ND-COOH and ND-LYS) out of the five nanodiamond-based matrices studied. ND-SA gave a weak signal while ND-LYS gave an intense peak. Without the addition of potassium ions, the 483 Da [M+K]⁺ signal was observed when ND-DHB was used. In addition to the [M+H]⁺ signal, ND-COOH also gave a weak m/z 467 [M+Na]⁺ peak. When conventional matrices were used, SA and CHCA gave an intense [M+H]⁺ signal, while DHB showed an intense m/z 483 Da [M+K]⁺ peak (without the addition of potassium ions). CHCA also showed a moderate m/z [M+Na]⁺ peak. The nanodiamond-based matrices gave a good [M−H]⁻ peak signal and poor [M+H]⁺ signal in the positive mode, which was contrary to the conventional matrices.

C. Analysis of Erythromycin (ER) [733 Da]

Negative Ion Mode:

In the negative ion mode, [M−H]⁻ ions (m/z 732 Da) were detected when each of the nanodiamond-based matrices was used. ND-COOH, ND-CHCA and ND-DHB gave a weak [M−H]⁻ signal, while both ND-LYS and ND-SA showed intense peaks, with low background and no inference from the matrix signals. The m/z 732 [M−H]⁻ ions were not observed in the three conventional matrices. The spectra from the three conventional matrices were also characterized by a large amount of background noise and peak interference.

Positive Ion Mode:

The m/z 734 Da [M+H]⁺ ion peak was not observed when the nanodiamond-based matrices were used. However, without the addition of sodium or potassium ions, the use of all five (ND-SA, ND-CHCA, ND-COOH, ND-DHB and ND-LYS) nanodiamond-based matrices gave m/z 756 [M+Na]⁺ and 772 [M+K]⁺ ion peaks, with the m/z 756 signal always higher than the m/z 772 signal in ion count intensity. ND-LYS gave the most intense signal amongst all of the nanodiamond-based matrices used in the present studies. A similar observation was noted with the conventional matrices, where all three matrices gave moderate to very intense m/z 756 [M+Na]⁺ and 772 [M+K]⁺ ion peaks. All spectra obtained with the nanodiamond-based matrices had less background noise than conventional matrices with no peak interference than conventional matrices.

D. Analysis of Quinine (QN) [324 Da]

Negative Ion Mode:

Under the same conditions, analysis of quinine (QN [324 Da]) consistently revealed, with strong intensity, an m/z [M−H₂—H]⁻ ion (321 Da) for all of the nanodiamond-based matrices and the conventional organic matrices, except for CHCA, which gave no signal at all.

Positive ion Mode:

No m/z 325 [M+H]⁺ was observed with all the matrices (both ND-based and conventional). Instead, m/z 363 [M+K]⁺ and 347 [M+Na]⁺ were observed when ND-CHCA and DHB were used, respectively.

E. Analysis of Prednisolone (PD) [360 Da]

Negative Ion Mode:

All spectra obtained using a nanodiamond-based matrix showed an intense signal of the desired m/z 359 [M−H]⁻ ion peak with low background noise. Among the conventional matrices, SA and DHB gave an intense peak while CHCA gave a very weak signal with a significant amount of background interference.

Positive Ion Mode:

The m/z 361 [M+H]⁺ peak was not observed in spectra obtained using any of the nanodiamond-based matrices. However, without the addition of sodium or potassium ions, all five nanodiamond-based matrices (ND-SA, ND-CHCA, ND-COOH, ND-DHB and ND-LYS) gave m/z 383 [M+Na]⁺ and 399 [M+K]⁺399 ion peaks, with the m/z 383 signal always higher than the m/z 399 in ion count intensity. ND-LYS gave the most intense signal amongst each of the nanodiamond-based matrices studied. Among the conventional matrices, SA showed an intense m/z 361 Da [M+H]⁺ peak only, DHB showed the m/z 383 Da [M+Na]⁺ peak in addition to the m/z 361 Da [M+H]⁺ peak and lastly, CHCA showed m/z 383 Da [M+Na]⁺ and m/z 399 Da [M+K]⁺ peaks. All spectra obtained with the nanodiamond-based matrices had less background noise and no detectable peak interference compared to the conventional matrices.

F. Analysis at D Different Laser Intensities

Table 4 shows the analysis of the above five analytes with the three conventional matrices (SA, CHCA and DHB) at the matrix's specific optimum laser intensity. Generally, it was noted that the nanodiamond-based matrices performed much better in the negative ion mode than the conventional matrices and vice versa.

G. Other Analytes

The five other analytes shown in Table 1 (melphalan, hesperetine luteolin-7-O-glucoside and leucine-enkephalin) can also be analyzed using the covalently functionalized nanodiamond-based matrices of the present disclosure. Addition of TFA (for example, in the case of quinine) and introduction of larger counter ions such as K⁺ and Na⁺, in some cases can help improve the signal intensity in the positive ion mode.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE SPECIFICATION

[1] Cohen, L., E. P. Go, and G. Suizdak, *Small-Molecules Desorption/Ionization Mass Analysis*. MALDI MS, ed. F. Hillenkamp and J. Peter-Katalinic. 2007: John Willey and Sons. 345 (299-337) New York.

[2] Cohen, L. and A. I. Gusev, *Small molecule analysis by MALDI mass spectrometry*. Anal. Bioanal. Chem. 2002, 373, 571-586.

[3] Schrand, A. M., S. A. C. Hens, and O. A. Shenderova, *Nanodiamond particles: Properties and perspectives for bioapplications*. Critical Reviews in Solid State and Materials Sciences, 2009. 34(1-2): p. 18-74.

[4] Mochalin, V. N., et al., *The properties and applications of nanodiamonds*. Nature Nanotechnology, 2012. 7(1): p. 11-23.

[5] Wagner, Ingrid; Musso, Hans (November 1983). "New Naturally Occurring Amino Acids". *Angew. Chem. Int. Ed. Engl.* 22 (22): 816-828.

[6]. Kaur, R., J. M. Chitanda, D. Michel, J. Maley, F. Borondics, P. Yang, R. E. Verrall and I. Badea, "Lysine-functionalized nanodiamonds: synthesis, physiochemical characterization, and nucleic acid binding studies" *International Journal of Nanomedicine* 2012, 7, 3851-3866.

TABLE 1
Analytes
PIROXICAM (PX)
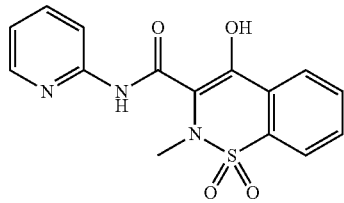
Chemical Formula: $C_{15}H_{13}N_3O_4S$
Exact Mass: 331.06
Molecular Weight: 331.35
TETRACYCLINE (TC)
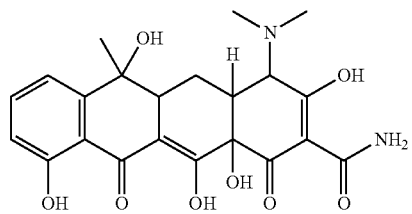
Chemical Formula: $C_{22}H_{24}N_2O_8$
Exact Mass: 444.15
Molecular Weight: 444.43
ERYTHROMYCIN
(ER)
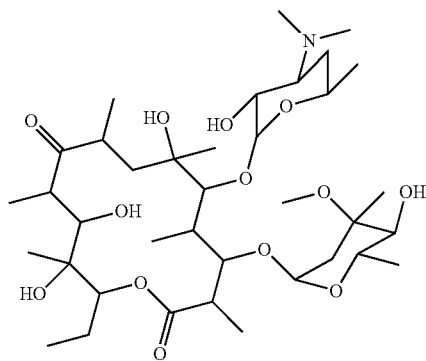
Chemical Formula: $C_{37}H_{67}NO_{13}$
Exact Mass: 733.46
Molecular Weight: 733.93
QUININE (QN)
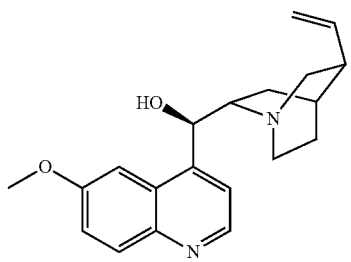
Chemical Formula: $C_{20}H_{24}N_2O_2$
Exact Mass: 324.18
Molecular Weight: 324.42

TABLE 1-continued
Analytes
PREDNISOLONE
(PD)
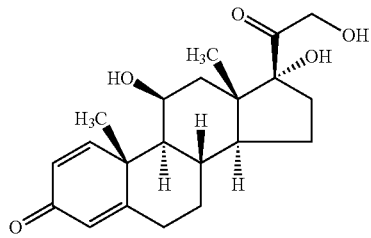
Chemical Formula: $C_{21}H_{28}O_5$
Exact Mass: 360.19
Molecular Weight: 360.44
MELPHALAN (MP)
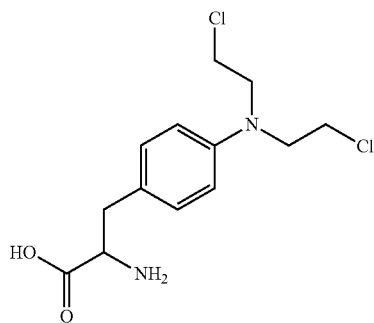
Chemical Formula: $C_{13}H_{18}Cl_2N_2O_2$
Exact Mass: 304.07
Molecular Weight: 305.20
HESPERETINE (HP)
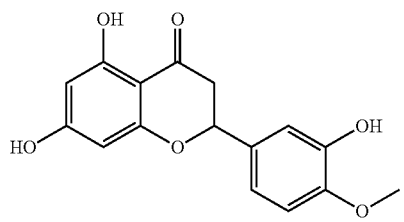
Chemical Formula: $C_{16}H_{14}O_6$
Exact Mass: 302.08
Molecular Weight: 302.28

TABLE 1-continued

Analytes

RESERPINE (RP)

Chemical Formula: $C_{33}H_{40}N_2O_9$
Exact Mass: 608.27
Molecular Weight: 608.68

LUECINE-ENKEPHALIN (LE)

Chemical Formula: $C_{28}H_{37}N_5O_7$
Exact Mass: 555.27
Molecular Weight: 555.62

LUTEOLIN-7-O-GLUCOSIDE

Chemical Formula: $C_{21}H_{20}O_{11}$
Exact Mass: 448.10
Molecular Weight: 448.38

TABLE 2

Analysis of five analytes using five nanodiamond-based matrices

| ANALYTE | MATRIX | | | | |
|---|---|---|---|---|---|
| | ND-SA | ND-CHCA | ND-COOH | ND-DHB | ND-LYS |
| Piroxicam (PX) | Negative Mode: moderate [M − H]⁻ Positive Mode: Intense [M + H]⁺ | Negative Mode: moderate [M − H]⁻ Positive Mode: weak [M + H]⁺ | Negative Mode: very Intense [M − H]⁻ Positive Mode: weak [M + H]⁺ | Negative Mode: moderate [M − H]⁻ Positive Mode: very weak [M + H]⁺ | Negative Mode: very Intense [M − H]⁻ Positive Mode: very weak [M + H]⁺ |
| Tetracycline (TC) | Negative Mode: Intense [M − H]⁻ 443 Da Positive Mode: very weak [M + H]⁺ 445 | Negative Mode: weak [M − H]⁻ 443 Da Positive Mode: weak [M + H]⁺ 445 | Negative Mode: Intense [M − H]⁻ Positive Mode: weak [M + H]⁺ 445, [M + Na]⁺ 467 | Negative Mode: Intense [M − H]⁻ Positive Mode: Intense [M + K]⁺ 483 | Negative Mode: very Intense [M − H]⁻ Positive Mode: Intense [M + H]⁺ 445 |

TABLE 2-continued

Analysis of five analytes using five nanodiamond-based matrices

| ANALYTE | MATRIX | | | | |
|---|---|---|---|---|---|
| | ND-SA | ND-CHCA | ND-COOH | ND-DHB | ND-LYS |
| Erythromycin (ER) | Negative Mode: Intense [M − H]⁻ Positive Mode: Intense [M + Na]⁺ 756 and [M + K]⁺ 772 | Negative Mode: weak [M − H]⁻ Positive Mode: Intense [M + Na]⁺ 756 and [M + K]⁺ 772 | Negative Mode: weak [M − H]⁻ Positive Mode: Intense [M + Na]⁺ 756 and [M + K]⁺ 772 | Negative Mode: weak [M − H]⁻ Positive Mode: Intense [M + Na]⁺ 756 and [M + K]⁺ 772 | Negative Mode: Intense [M − H]⁻ Positive Mode: very Intense [M + Na]⁺ 756 and [M + K]⁺ 772 |
| Quinine (QN) (324) | Negative Mode: Intense [M − H₂ − H]⁻ 321 Positive Mode: No Signal | Negative Mode: Intense [M − H₂ − H]⁻ 321 Positive Mode: Intense [M + K]⁺ 363 | Negative Mode: weak [M − H₂ − H]⁻ 321 Positive Mode: No Signal | Negative Mode: Intense [M − H₂ − H]⁻ 321 Positive Mode: No Signal | Negative Mode: weak [M − H₂ − H]⁻ 321 Positive Mode: No Signal |

TABLE 2-continued

Analysis of five analytes using five nanodiamond-based matrices

| ANALYTE | MATRIX | | | | |
|---|---|---|---|---|---|
| | ND-SA | ND-CHCA | ND-COOH | ND-DHB | ND-LYS |
| Prednisolone (PD) | Negative Mode: Intense [M − H]⁻ 359 Positive Mode: Intense [M + Na]⁺ 383 and [M + K]⁺ 399 | Negative Mode: Intense [M − H]⁻ 359 Positive Mode: Intense [M + Na]⁺ 383 and [M + K]⁺ 399 | Negative Mode: Intense [M − H]⁻ 359 Positive Mode: Intense [M + Na]⁺ 383 and [M + K]⁺ 399 | Negative Mode: Intense [M − H]⁻ 359 Positive Mode: Intense [M + Na]⁺ 383 and [M + K]⁺ 399 | Negative Mode: Intense [M − H]⁻ 359 Positive Mode: very Intense [M + Na]⁺ 383 and [M + K]⁺ 399 |

Key: Very intense ≥ 10⁵, intense ≥ 10⁴, moderate ≥ 10³, weak ≥ 10², very weak ≤ 10² ion count

TABLE 3

Analysis of five analytes using three conventional matrices

| | SA | CHCA | DHB |
|---|---|---|---|
| 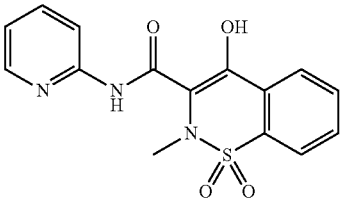 Piroxicam | Negative Mode: weak [M − H]− Positive Mode: Intense [M + H]+ | Negative Mode: No Signal Positive Mode: Intense [M + H]+ | Negative Mode: No Signal Positive Mode: Intense [M + H]+ |
| 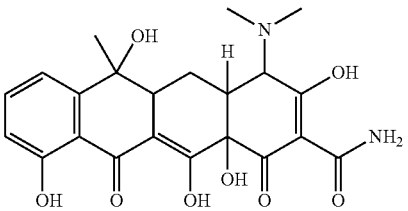 Tetracycline | Negative Mode: Intense [M − H]− Positive Mode: Intense [M + H]+ | Negative Mode: No Signal Positive Mode: Intense [M + H]+ Moderate [M + Na]+ | Negative Mode: very weak [M − H]− Positive Mode: Intense [M + K]−+ |
| 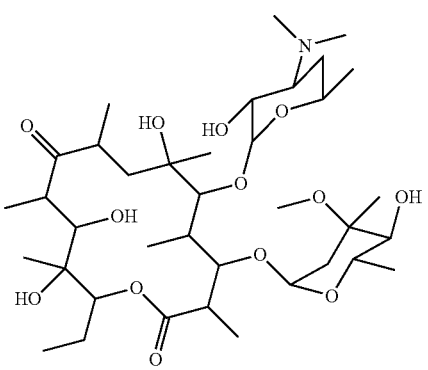 Erythromycin | Negative Mode: No signal detected Positive Mode: Moderate [M + Na]+ and [M + K]+ | Negative Mode: No signal detected Positive Mode: Intense [M + Na]+ and [M + K]+ | Negative Mode: No signal detected Positive Mode: very Intense [M + Na]+ and [M + K]+ |
| 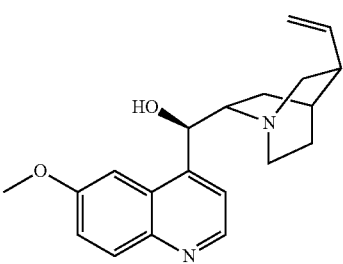 Quinine | Negative Mode: Intense [M − H]− 321 Positive Mode: No signal] | Negative Mode: No Signal Positive Mode: No Signal | Negative Mode: Intense [M − H]− 321 Positive Mode: Weak [M + Na] 347 |
| 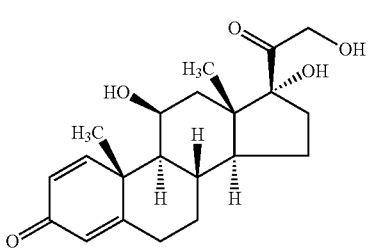 Prednisolone | Negative Mode: Intense [M − H]− Positive Mode: Intense [M + H]+ 361 | Negative Mode: Intense [M − H]− Positive Mode: Intense [M + Na]+ 383 [M + K]+ 399 | Negative Mode: very weak [M − H]− Positive Mode: Intense [M + H]+ 361 [M + Na]+ 383 |

Key: Very intense ≥ $10^5$, intense ≥ $10^4$, moderate ≥ $10^3$, weak ≥ $10^2$, very weak ≤ $10^2$ ion count

TABLE 4

Analysis of five analytes using three traditional matrices at lower laser intensity

| Analyte | Matrix | | |
|---|---|---|---|
| | SA<br>Laser intensity =<br>3500-4400 | CHCA<br>Laser intensity =<br>2800-3200 | DHB<br>Laser intensity =<br>4000-4700 |
| Piroxicam | Negative Mode:<br>Weak to Moderate<br>$[M - H]^-$ 330<br>Positive Mode:<br>Moderate $[M + H]^+$ | Negative Mode:<br>No signal<br>Positive Mode:<br>Very Intense $[M + H]^+$ | Negative Mode:<br>No signal<br>Positive Mode:<br>intense $[M + H]^+$ |
| Tetracycline | Negative Mode:<br>No signal<br>Positive Mode:<br>Very weak $[M + H]^+$ | Negative Mode:<br>No signal<br>Positive Mode:<br>Intense $[M + H]^+$<br>moderate $[M + Na]+$ | Negative Mode:<br>No signal<br>Positive Mode:<br>Intense $[M + H]^+$ moderate<br>$[M + Na]^+$, weak $[M + K]^+$ |
| Erythromycin | Negative Mode:<br>No signal<br>Positive Mode:<br>No signal-low ion<br>count | Negative Mode:<br>No signal<br>Positive Mode: Intense<br>$[M + Na]^+$ weak$[M + K]^+$ | Negative Mode:<br>No signal<br>Positive Mode:<br>Moderate $[M + Na]^+$<br>weak $[M + K]^+$ |
| Quinine | Negative Mode:<br>Very weak $[M - H]^-$<br>Positive Mode:<br>No signal | Negative Mode:<br>weak $[M - H]^-$<br>Positive Mode:<br>No signal | Negative Mode:<br>No signal<br>Positive Mode:<br>Moderate $[M + Na]^+$ |

TABLE 4-continued

Analysis of five analytes using three traditional matrices at lower laser intensity

| Analyte | Matrix | | |
|---|---|---|---|
| | SA<br>Laser intensity =<br>3500-4400 | CHCA<br>Laser intensity =<br>2800-3200 | DHB<br>Laser intensity =<br>4000-4700 |
| 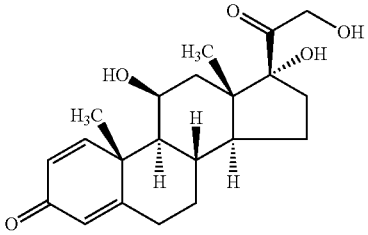<br>Prednisolone | Negative Mode:<br>No signal<br>Positive Mode:<br>No signal | Negative Mode:<br>No signal<br>Positive Mode:<br>Moderate [M + K]$^+$ | Negative Mode:<br>Intense [M − H]$^−$<br>Positive Mode:<br>Moderate [M + K]$^+$ and<br>[M + H]$^+$ |

Key: Very intense ≥ 10$^5$, intense ≥ 10$^4$, moderate ≥ 10$^3$, weak ≥ 10$^2$, very weak ≤ 10$^2$ ion count

The invention claimed is:

1. A functionalized nanodiamond comprising at least one compound that is MALDI matrix covalently linked to a nanodiamond.

2. The functionalized nanodiamond of claim 1, wherein the MALDI matrix is covalently linked to the nanodiamond via an ester linkage.

3. The functionalized nanodiamond of claim 1, wherein the MALDI matrix is covalently linked to the nanodiamond via an amide linkage.

4. The functionalized nanodiamond of claim 1, wherein the compound that is a MALDI matrix is selected from a cinnamic acid, a hydroxylated benzoic acid derivative, an aromatic carbonyl derivative, an aromatic amine, an aliphatic amine, a naturally occurring amino acid, an analog of a naturally occurring amino acid, a derivative of a naturally occurring amino acid, a peptide comprising 2 to 10 naturally occurring amino acids, a peptide comprising 2 to 10 naturally occurring amino acids of which at least one is an analog of a naturally occurring amino acid and a peptide comprising 2 to 10 naturally occurring amino acids of which at least one is an derivative of a naturally occurring amino acid, or, where possible, a salt thereof.

5. The functionalized nanodiamond of claim 1, wherein the compound that is a MALDI matrix is selected from the group consisting of sinapinic acid (3,5-dimethoxy-4-hydroxycinnamic acid), α-cyano-4-hydroxycinnamic acid, 2,4-dihydroxybenzoic acid, 2,6-diamino-N-(3-aminopropyl)hexanamide, 2,5-dihydroxybenzoic acid, nicotinic acid, ferulic acid (4-hydroxy-3-methoxycinnamic acid), caffeic acid, 3-hydroxypicolinic acid, picolinic acid, 2-amino-4-methyl-5-nitropyridine, 2-amino-5-nitropyridine, 2-iodoacetamide, 2,4,6-trihydroxyacetophenone, 2,6-dihydroxyacetophenone, 1,5-diaminonaphthalene, 2-(4'-hydroxybenzeneazo)benzoic acid, 2-mercaptobenzothiazole, 4-chloro-α-cyanocinnamic acid and α-cyano-4-fluorocinnamic acid.

6. The functionalized nanodiamond of claim 1, wherein the compound that is a MALDI matrix is a naturally occurring amino acid or an analog or derivative of a naturally occurring amino acid, or a salt thereof.

7. The functionalized nanodiamond of claim 6, wherein the naturally occurring amino acid is a naturally occurring basic amino acid, or an analog or derivative of a naturally occurring basic amino acid, or an acid addition salt thereof.

8. The functionalized nanodiamond of claim 7, wherein the naturally occurring basic amino acid is selected from histidine and lysine, and an analog or derivative thereof, or an acid addition salt thereof.

9. The functionalized nanodiamond of claim 1, wherein the compound that is a MALDI matrix is a naturally occurring dipeptide or an analog or derivative of a naturally occurring dipeptide, or a salt thereof.

10. The functionalized nanodiamond of claim 9, wherein the naturally occurring dipeptide comprises at least one naturally occurring basic amino acid, or an analog or derivative of a naturally occurring basic amino acid, or an acid addition salt thereof.

11. The functionalized nanodiamond of claim 10, wherein the naturally occurring basic amino acid is selected from histidine and lysine, and an analog or derivative thereof, or an acid addition salt thereof.

12. The functionalized nanodiamond of claim 6, wherein the compound that is a MALDI matrix is covalently linked to the nanodiamond via a linker group.

13. The functionalized nanodiamond of claim 9, wherein the compound that is a MALDI matrix is covalently linked to the nanodiamond via a linker group.

14. The functionalized nanodiamond of claim 1, wherein the nanodiamond is a detonated nanodiamond which has been treated under oxidative or reductive conditions.

15. The functionalized nanodiamond of claim 14, wherein the nanodiamond is a detonated nanodiamond which has been treated under oxidative conditions to provide a carboxylated nanodiamond (ND-COOH).

16. The functionalized nanodiamond of claim 1, wherein the nanodiamond has a diameter of about 1 nm to about 10 nm, about 3 nm to about 6 nm or about 4 nm to about 5 nm.

17. A nanodiamond-based composition comprising one or more of the functionalized nanodiamonds of claim 1.

18. The composition of claim 17, wherein the nanodiamond-based composition is a MALDI-MS composition.

19. A method of performing MALDI-MS, comprising
a) depositing (1) a nanodiamond-based composition of claims 18, and (2) a sample on a MALDI substrate; and
b) performing MALDI-MS.

20. The method of claim 19, wherein the sample comprises, consists essentially of or consists of at least one analyte that is a small molecule.

* * * * *